United States Patent [19]
Volk

[11] Patent Number: 5,200,773
[45] Date of Patent: Apr. 6, 1993

[54] DIAGNOSTIC INDIRECT OPHTHALMOSCOPY CONTACT LENS SYSTEM

[76] Inventor: Donald A. Volk, 9378 Jackson Ave., Mentor, Ohio 44060

[21] Appl. No.: 604,531

[22] Filed: Oct. 29, 1990

Related U.S. Application Data

[63] Continuation-in-part of Ser. No. 428,504, Oct. 27, 1989, Pat. No. 5,046,836.

[51] Int. Cl.⁵ ............................................. A61B 3/00
[52] U.S. Cl. .................................. 351/219; 351/160 R
[58] Field of Search .................... 351/219, 205, 160 R

[56] References Cited

U.S. PATENT DOCUMENTS

4,410,245 10/1983 Koester .............................. 351/219
4,728,183 3/1988 Heacock et al. .................... 351/219

*Primary Examiner*—Rodney B. Bovernick
*Attorney, Agent, or Firm*—Oldham, Oldham, & Wilson Co.

[57] ABSTRACT

A diagnostic indirect ophthalmoscopy lens device utilized for illumination and observation of the fundus of the eye may include a plus powered aspheric contact element and at least one anterior lens element which may also have aspheric surfaces and/or positive refractive power. The lens elements in combination act to illuminate and form an inverted aerial image of the fundus of the eye. A erecting optical system may be provided to reinvert the image produced by the lenses of the device, which facilitates examining or surgical procedures. The device may be a hand held device to enable easy manipulation, or may be a non-hand held device which maintains its position on the eye to be examined. The device may further include a separate source of illuminating light which allows proper illumination of the eye while avoiding reflections or the like.

20 Claims, 6 Drawing Sheets

DIAGNOSTIC INDIRECT OPHTHALMOSCOPY CONTACT LENS SYSTEM

BACKGROUND OF THE INVENTION

This application is a Continuation-in-Part of copending U.S. Pat. application Ser. No. 428,504 filed Oct. 27, 1989, now U.S. Pat. No. 5,046,836.

The present invention relates to a diagnostic indirect ophthalmoscopy contact lens device. More particularly, the invention relates to a diagnostic contact lens for indirect ophthalmoscopy which operates both as an improved condensing lens device for conveyance of a light from an indirect ophthalmoscope or slit lamp biomicroscope through the pupil and onto the fundus of an examined eye. The lens device also acts to form a aberration free and extremely wide field inverted or upright real aerial image of the fundus of the eye.

Diagnostic lenses for indirect ophthalmoscopy are used by ophthalmologists and optometrists to observe the fundus of an eye for diagnostic or surgical procedures. Various known ophthalmoscopic lenses or other diagnostic devices, have lenses for conveying light from a source onto the fundus of an eye and forming an aerial image of the fundus. In U.S. Pat. No. 3,954,329, there is shown an ophthalmoscope for viewing a fundus which includes a contact lens which directly contacts the cornea of the eye as well as a posterior or field lens spaced from the contact lens and supported in a housing relative thereto. This invention employs both direct illumination of the fundus of the eye as well as transillumination to obtain wide angle viewing of the fundus. Other similar systems in U.S. Pat. Nos. 4,265,519 and 3,994,341 show various illumination techniques and lens systems for ophthalmoscopes and fundus cameras. An indirect ophthalmoscopy lens for use with a slit lamp biomicroscope is disclosed in U.S. Pat. No. 4,627,694.

More recently, indirect ophthalmoscopy has been utilized in laser microsurgery techniques to enable the ophthalmologists to obtain a wide angle image of the fundus as well as to convey the laser beam to the fundus accurately. In an attempt to provide wide angle viewing of the fundus without aberration, U.S. Pat. No. 4,728,182 to Heacock utilizes a contact lens element situated relative to an entry lens in a holder. It is stated that the contact lens element is designed such that the light rays emerging from the patient's eye exit the contact lens in a parallel relationship which are then directed to the entry lens. The entry lens is an aspheric lens which forms an aerial image of the fundus.

This patent thus describes an ophthalmic lens system wherein the contact lens has two spherical surfaces, designed such that light rays emerging from the patient's eye and through the contact lens are substantially parallel, rather than convergent, as they exit in an anterior direction from the contact lens. In this design, the aspheric entry lens of this invention will be inadequate in some circumstances as an image forming lens as it will be insufficient for correcting field curvature and aberrations due in part to the spherical design of the contact lens. The contact lens design has failed to account for the corrective quality of the aspheric cornea of the eye itself and may tend to degrade the image of the fundus of the eye. It is also desired to form an extremely wide field image of the fundus of the eye using a diagnostic contact lens system to enable the ophthalmologist and optometrist to view more of the fundus for proper and easier diagnosis. In the invention of Heacock as well as other prior art inventions, mirrors are sometimes interposed between the contact lens and entry lens of the system to increase the field of view of the fundus. The addition of mirrors into the system adds complexity, costs and may tend to degrade the quality of the image. Even with the use of mirrors it may still be necessary to move the lens on the examined eye.

In a similar manner, the indirect ophthalmoscopy diagnostic contact lens system should function as a condensing lens for converging light from the light source of a biomicroscope through the pupil of an examined eye onto the fundus of the eye. In order to obtain an aberration free, focused image of the light source, such as in a slit lamp biomicroscope or other ophthalmoscope, the lens system should provide the optical properties to avoid aberrations normally associated with spherical lenses.

Embodiments of the optical system of the present invention has the unique feature that the aerial image of the fundus produced by it is an upright image rather than an inverted image as has normally been formed with prior art indirect ophthalmoscopy lenses. It should be recognized that viewing of an inverted aerial image will require the examiner to mentally reorient what is observed to correspond to the actual position of the parts of the fundus being viewed. The observation of an inverted image may thus be confusing to an ophthalmologist who may be treating a retinal lesion or tumor, and is extremely disadvantageous in surgical techniques such as vitrectomy. One device utilized for indirect ophthalmoscopy which generates an upright image is set forth in U.S. Pat. No. 4,721,378, but the optical characteristics are somewhat less than desirable to achieve the proper optical characteristics requires special lenses of the like.

It is also noted that prior art indirect ophthalmoscopy devices which are used with the indirect ophthalmoscope or slit lamp biomicroscope, are positioned in front of the eye which is binocularly viewed by the biomicroscope. The illumination system of the biomicroscope is thus made to pass through the indirect ophthalmoscopy device wherein the device should converge the illuminating light for proper illumination of the fundus. With such a system, it should be apparent that various reflections or glare may be produced by the illumination system of the biomicroscope. Various alternative illumination techniques may be utilized to prevent the formation of reflections or the like, but such techniques may not suitably illuminate the fundus of the eye or entail implantation of illuminating devices into the eye.

SUMMARY OF THE INVENTION

There has therefore been found a need to provide a diagnostic contact lens for indirect ophthalmoscopy which has superior optical performance and produces an extremely wide field of view and forms an image substantially free of aberrations. The lens system should function both as an improved condensing lens converging light from a light source and for forming a clear and focused image of the fundus of the eye.

It is therefore a main object of the present invention to provide a diagnostic indirect ophthalmoscopy device which corrects optical aberrations or distortions relating to its functioning simultaneously as an improved condensing lens system for converging light from a biomicroscope or ophthalmoscope light source onto the fundus of an examined eye as well as an improved image forming lens for the fundus of the eye.

It is another object of this invention to provide a diagnostic indirect ophthalmoscopy device utilizing at least two optical elements which may have aspheric surfaces and/or positive refractive power.

It is another object of this invention to provide a diagnostic indirect ophthalmoscopy device producing an extremely wide field of view of the fundus of the eye.

It is another object of this invention to provide a contact lens element in association with at least a biconvex anterior lens element wherein the lens elements work in conjunction with one another to enable correction of optical aberrations degrading the aerial image of the fundus of the image of the aperture of the light source of a biomicroscopy or ophthalmoscopy projects by the lens of this invention onto the fundus of any eye.

It is another object of this invention to provide a contact lens element which may have an aspheric anterior surface for correction of optical aberrations degrading the aerial image of the fundus or the image of the aperture of the light source of a biomicroscope projected by the lens of this invention onto the fundus of an eye.

It is another object of this invention to provide an aspheric anterior surface on contact lens element enabling utilization of very short apical radii and relatively large diameters.

It is another object of this invention to provide an aspheric anterior surface on an aspheric contact element enabling utilization of relatively large diameters.

It is another object of this invention to provide an aspheric posterior surface on an aspheric contact element and means for facilitating translational movement of the lens of this invention on the cornea of an eye under examination.

It is another object of this invention to provide means for securing and interconnecting the lens elements of the relative to one another within an easily manipulable housing which may provide a hand-held device or a device which will be positioned for indirect ophthalmoscopy without being hand-held.

It is another object of this invention to provide means for laser delivery to the far peripheral as well as the central fundus of an examined eye.

Yet another object of the invention is to provide a diagnostic indirect ophthalmoscopy device which will form an upright aerial image of the fundus of the eye which is substantially aberration free.

It is yet another object of the invention to provide a diagnostic indirect ophthalmoscopy device which will form a substantially aberration free aerial image of the eye to conduct vitrectomy, or the like, wherein the lens device is positioned to form the aerial image without being hand-held.

Another object of the invention is to provide a diagnostic indirect ophthalmoscopy device which may include a separate means of illumination so as to reduce reflections which may be created by the illumination system of the ophthalmoscope or biomicroscope.

Yet another object of the invention is to provide a diagnostic indirect ophthalmoscopy device which may include a contact lens element and a plurality of anterior lens elements which act in conjunction with one another to form a substantially aberration free aerial image of the fundus of the eye which may be inverted or upright, as well as forming an improved condensing lens system for converging light onto the fundus of the eye.

The objects of the invention are accomplished by an improved diagnostic contact lens for indirect ophthalmoscopy which simultaneously functions as both an improved condensing lens as well as an improved image forming lens. The lens system acts to converge light from the source of a slit lamp biomicroscope or other microscope through the pupil of an examined eye, projecting a distortion free, clear and focused image of the aperture of the light source on to the fundus of an examined eye. The lens system also produces an extremely wide field upright or inverted real aerial image of the fundus of the eye which is essentially free of field curvature, lateral astigmatism and distortion, viewed either monocularly or binocularly through an ophthalmoscope or biomicroscope.

The invention may include a corneal contact element which may have aspheric surfaces and positive refractive power, at least one biconvex anterior lens which may also have aspheric surfaces and positive refractive power, and a housing securing and interconnecting the lens components while preventing extraneous light, moisture, and dirt from entering the interior optical area. The device may be a hand-held unit which is easily manipulable by the physician or a non-hand-held unit which is positionable to conduct indirect ophthalmoscopy while maintaining its position unaided. The preferred embodiment includes a contact element with an aspheric anterior surface that not only contributes to the improved optical performance of the unit as both a condensing lens and image forming lens, but in addition, because of the continuous and progressive reduction in curvature peripheralward, allows for surfaces with both short apical radii and relatively large diameters. The concave posterior surface of the contact element may also be aspheric, thereby, facilitating an improved corneal fit as well as translational movement of the lens unit on the eye. One or more biconvex anterior elements may also include aspheric surfaces to co-act with the aspheric contact element in such a way as to provide optimum condensing and image forming properties. It is desired that each of the two or more lens elements have significant light converging properties and be aspheric, and it is these features in addition to others that distinguish it from the prior art lenses and which provide improved performance and high optical resolution. The anterior lens element(s) may be very high powered lenses which allow for an extremely wide field of view as desired. In a hand-held unit, the anterior lens element may have a refractive power chosen to optimize the field of view obtainable by the device in conjunction with the contact lens element. Alternatively, it a non-hand-held unit, the dimensions of the device are extremely critical for maintaining the position of the device to enable indirect ophthalmoscopy without requiring manipulation by the physician. In such an embodiment, an extremely high powered lens may be utilized to maximize the field of view in accordance with the dimensions of the device. An upright aerial image may be formed by the diagnostic indirect ophthalmoscopy device by utilizing coaxial anterior lenses having refractive powers to enable reinverting the image formed by a combination of the lenses in the device. Alternatively, an upright image may be formed by means of a reinverting prism structure associated with the device. To reduce reflection and glare in the aerial image, it may be desirable to provide a separate means to illuminate the fundus of the eye, wherein illuminating light may be provided in conjunction with the device so as to reduce the formation of reflections but to provide proper illumination of the fundus of the eye.

BRIEF DESCRIPTION OF THE DRAWINGS

The objects and advantages of the invention will become apparent as the detailed description of the invention proceeds with reference to the accompanying drawings, wherein.

DETAILED DESCRIPTION OF THE INVENTION

Figures 1, 2:
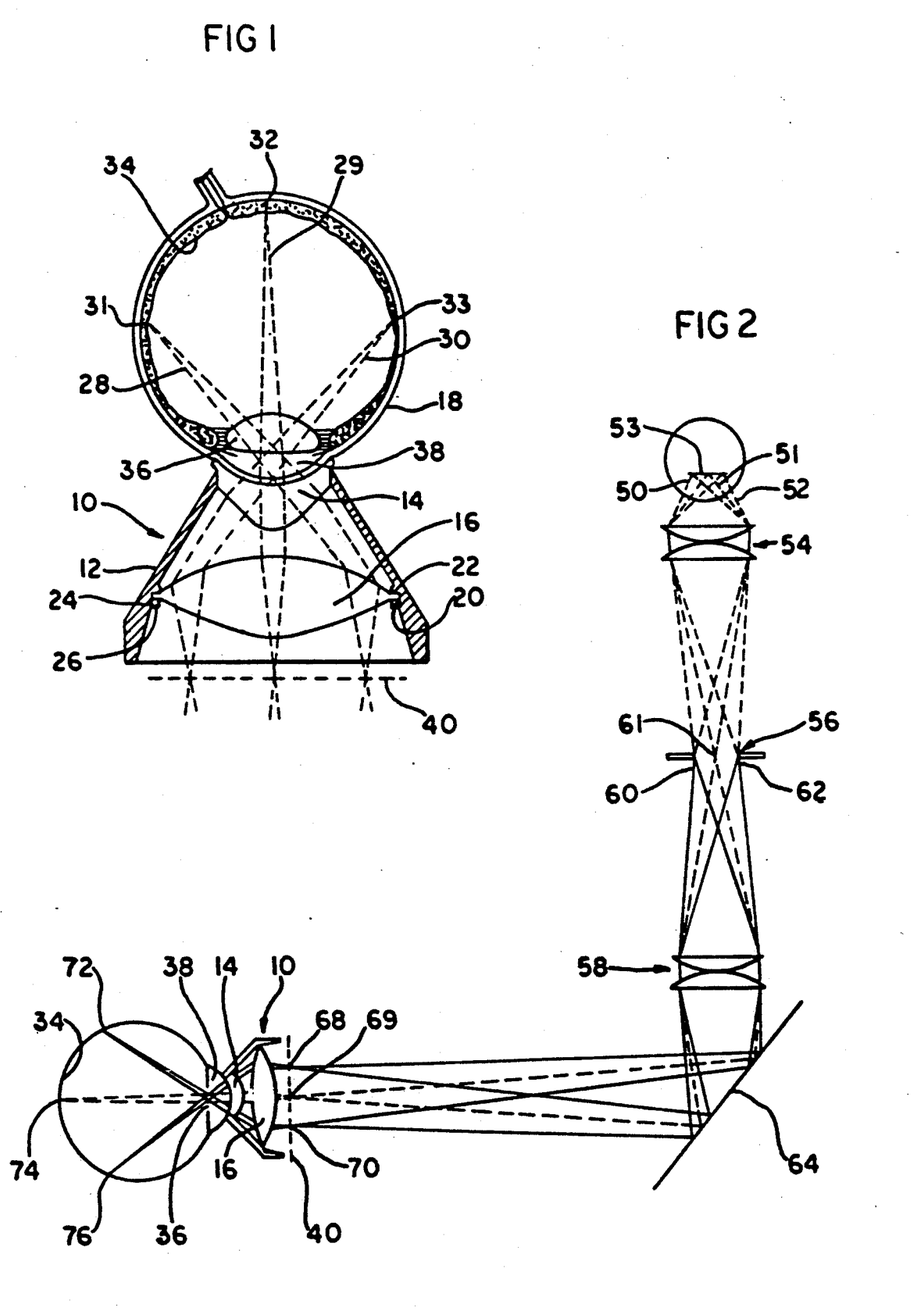
FIG. 1 is a schematic plan view of the indirect ophthalmoscopy diagnostic contact lens system of the invention.
FIG. 2 is a schematic plan view of the light path from a light source of a biomicroscope through the lens system of the invention onto the examined eye.

Referring now to FIG. 1, the compound diagnostic indirect ophthalmoscopy contact lens 10 includes a generally conically shaped lens holder 12, providing means for securing and interconnecting a contact lens element 14 and at least one anterior lens element 16. The lens holder 12 also allows a means for digital manipulation of the unit when disposed against the eye 18 of the patient. Both the contact lens element 14 and the anterior element 16 may be made of homogenous transparent optical material, such as glass or plastic. The optical material may be treated to include light filtering properties for absorbing specific wavelengths of light, or other known treatment to obtain the desired optical properties. It is preferred for safety purposes that the contact lens element 14 be made of ophthalmic plastic, such as poly methyl methacrylate or cr-39, and that the anterior element 16 be made of optical glass, such as Schott BK7.

The contact lens element 14 is mounted in the small end of the housing unit 12 so as to extend outwardly therefrom to enable contact with the cornea of the eye. The anterior lens element 16 is mounted in the larger diameter end of housing 12 inwardly of the open end to protect the lens. Both surfaces of the anterior lens element 16 and the anterior surface of the contact lens element 14 may be coated with an anti-reflective coating to minimize reflections and increase light transmission. The contact lens element 14 may be secured in place with optical glue, by means of interlocking threads, or by other conventional means. The interior portion of the larger diameter end of the conically shaped housing includes a generally cylindrical portion 20 which is approximately 0.003" larger in diameter than the diameter of the anterior lens 16. The portion 20 provides a cylindrical cavity into which the anterior lens 16 may be fitted and with a secondary cylindrical inner diameter 22, approximately 0.040" smaller than the diameter of the anterior lens 16, providing a shoulder on which the outer edge of the lens 16 is supported and spaced from the contact lens element 14. The depth of the primary cylinder is adequate to provide protection for the anterior surface of the anterior lens 16 when affixed against the secondary cylindrical shoulder. The primary cylinder may be internally threaded at 24 to receive an externally threaded retaining ring 26 securing the anterior lens 16 in place against the secondary cylindrical shoulder 22. The threaded retaining ring systems are standard conventional means by which optical lenses are secured in lens housings.

In the preferred embodiment of the invention, the contact element 14 and anterior element 16 both have positive refractive power and act in conjunction with one another to produce an extremely wide field of view of the fundus of an eye which is substantially free of optical aberrations. Additionally, the anterior element 16 is designed as a biconvex lens having predetermined refractive properties to coact with the plus powered contact element in such a way as to produce a condensing lens system for projection of light from a biomicroscope light source to produce a clear image of the light source aperture on the fundus of the eye. In the image forming function of the lens system 10, with light rays 28, 29 and 30 originating at and diverging from points 31, 32 and 33 respectively on the eye fundus 34 exit the eye through the pupil 36 and cornea 38 and are caused to converge by the contact lens element 14 towards the biconvex lens element 16 which additionally converges the rays to focus at image plane 40 anterior to the biconvex element 16.

Turning now to FIG. 2, the light ray paths of the illumination system of a conventional slit lamp biomicroscope when used in conjunction with the lens system of the present invention are shown. As mentioned earlier, the lens system of this invention has been designed to perform in an optimal fashion as a condensing lens for projecting a clear, sharply focused image of the aperture of the light source of a biomicroscope onto the fundus of an examined eye. In FIG. 2, light rays 50, 51 and 52 originating at a light source filament 53 are refracted by a condensing lens assembly 54 which directs the light rays towards the slit lamp aperture 56 which is situated at the back focus plane of condensing lens system 58. Functioning as a new light source at slit lamp aperture 56, light rays 60, 61 and 62 proceed toward and are refracted by condensing lens system 58 and continue toward mirror 64 which reflects the light rays at approximately 45 degrees towards the image plane 40 where the light rays form an aerial image of the slit lamp aperture 56. The image plane 40 functions as a new light source wherein light rays 68, 69 and 70 proceed to and are refracted by the aspheric biconvex lens 16. The anterior biconvex lens 16 being a plus powered lens causes the light rays 68, 69 and 70 to converge towards the contact lens element 14 of the device. The contact lens element 14 may also be plus powered and thus cause the light rays to further converge toward the pupil 36 of the examined eye through the cornea 38. The light rays proceed through the eye and are focused as a clear image of the slit lamp aperture 56 onto the fundus of the examined eye 34 at points 72, 74 and 76.

The condensing qualities of the lens system of the invention operate to transmit light rays from the light source onto the fundus of the eye without incurring optical aberrations which may be caused by typical lens systems. To minimize aberrations, the plus powered meniscus contact lens element 14 as well as at least one plus powered biconvex anterior lens element 16 each contribute positive refractive power to the optical system and may have aspheric surfaces which coact with one another in such a way to provide optimum condensing and image forming properties. The lens system provides significant light converging properties along with aspheric surfaces which optimize the optical system to avoid aberrations especially at the periphery of the formed image. The lens system also enables an extremely wide field of view and illumination so as to avoid the use of transillumination techniques or the like.

One of the novel features of this invention relates to the aspheric design of the contact lens element 14, where either the convex only or both the concave and convex surfaces are aspheric. The aspheric surfaces of revolution are of prolate type, decreasing in curvature from apex to periphery, and each of the two surfaces are on a common axis of revolution. An additional novel feature of this invention relates to the aspheric design of the biconvex lens element 16, where either or both the posterior and anterior surfaces are aspheric. The aspheric surfaces of the lens elements are defined by the polynomial:

$$y = (2rx + (e^2 - 1)x^2)^{\frac{1}{2}} + Ax^F + Bx^G + Cx^H.$$

The values of r, e, A, B, C, F, G, and H are chosen such that light rays originating at the fundus 34 of the eye, exiting through the pupil 36 of the eye and passing through the aspheric contact lens element 14 and biconvex aspheric lens element 16 form an aerial image of the fundus of the eye anterior to the aspheric biconvex element 16 at plane 40. The image is substantially free of aberrations such as field curvature, lateral astigmatism, and distortion.

In the preferred embodiment, the apical radius of curvature for each surface of the biconvex aspheric lens element 16 may range from 70 mm to 5 mm and may be in a reciprocal relationship with the apical radius of curvature of the opposite surface of element 16, ranging from 0.588 to 1.7 times its opposite surface radius value. For both front and back surfaces, values of e, representing apical eccentricity, may range from 0.7 to 4.0, coefficients A, B, C may range from −10.0 to 10.0, and exponents F, G, and H may range from 0.5 to 10.0. By selecting an anterior to posterior apical radius of curvature relationship of 1.6 to 1, and with the anterior surface polynomial utilizing the following parameters: r=9.887, e=1.3, A=0.022, B=−0.05, C=0.008, F=1.4, G=1.65, H=1.8, and with the posterior surface polynomial utilizing the following parameters: r=14.8305, e=2.6, A=−0.0210, B=0.028, C=−0.0118, F=1.4, G=1.65, H=1.8, the surfaces produced result in a biconvex lens element design ideal for contributing optimum condensing and image forming qualities to the lens system.

In the preferred embodiment, the contact lens element 14 has positive refractive power making it desirable to aspherize its convex anterior surface in order to minimize excess peripheral power and associated optical aberrations. The contact element 12 thereby aids the biconvex aspheric lens 14 in producing an aerial image free of aberrations. Additionally, the concave posterior surface of the contact lens 12 may be aspherized to closely approximate the aspheric corneal contour, with an apical radius of curvature substantially the same as that of the anterior surface of the average cornea. If the concave posterior surface is aspherized, it may be desirable to provide a peripheral slope of the lens which is equal to or less than that of the average cornea at an equivalent diameter, thereby minimizing the possibility of localized peripheral lens bearing and facilitating translational movement of the lens on the cornea. By having both surfaces of the contact element 12 aspheric, the beneficial optical properties resulting from aspherizing each surface are combined together.

Both the posterior and anterior surface curvatures of the contact lens element 14 may again be defined by the same polynomial:

$$Y = (2rx + (e^2 - 1)x^2)^{\frac{1}{2}} + Ax^F + Bx^G + Cx^H$$

where, for the convex anterior surface, values of r, e, A, B, C, F, G and H are chosen to satisfy optical correction based on the total refractive power of the contact element and the corresponding values of r, e, A, B, C, F, G, and H of the posterior concave surface. For the convex anterior surface, the apical radius of curvature, r, may range from 3.5 to 9.0, and e, representing apical eccentricity, may range from 0.05 to 1.4, coefficients A, B, and C may range from −10.0 to 10.0 and exponents F, G, and H may range from 0.5 to 10. For the concave posterior surface, the apical radius of curvature, r, may range from 6.5 to 9.0, and e, representing apical eccentricity may range from 0.0 to 1.2, coefficients A, B, C may range from −10.0 to 10.0 and exponents F, G, and H may range from 0.5 to 10. With the following parameters utilized for the convex anterior surface, r=6.9, e=0.685, A=−0.01, B=0.017, C=−0.0035, F=1.6, G=1.85, H=2.4, and the following parameters utilized for the concave posterior surface r=7.7, e=0.55, A=0.023, B=−0.018, C=0.002, F=2.5, G=2.8, H=3.7, the surfaces produced result in a contact element design ideal for a lens constructed in accordance with this invention.

Figure 3:
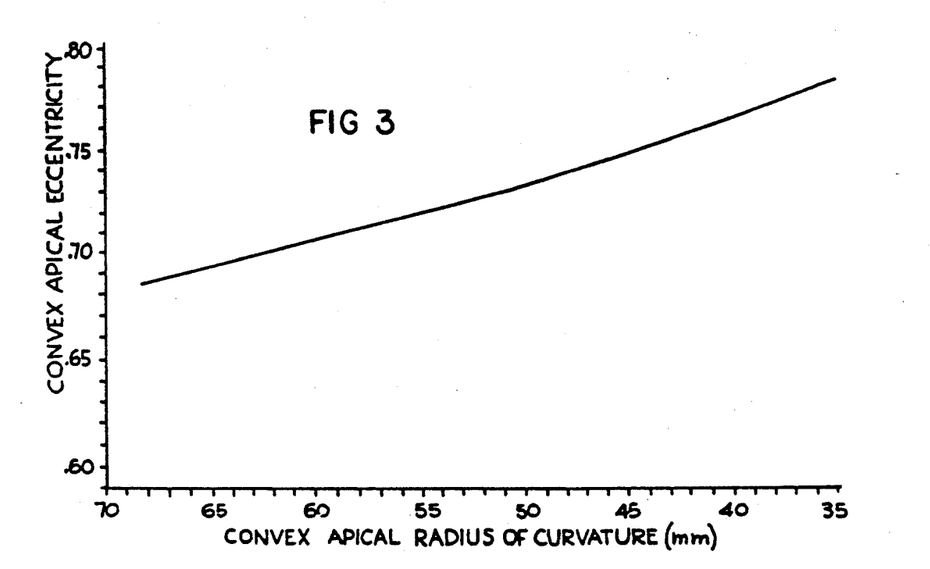
FIG. 3 is a plot of the convex apical eccentricity to the convex apical radius of curvature for the lens elements of the system.

Assuming the values of r, e, A, B, C, F, G, and H of the above example for the concave posterior surface, a graph plotting the range of apical radii of curvature of the aspheric convex anterior surface against corresponding values of e, eccentricity, for the aspheric convex anterior surface is shown in FIG. 3. Corresponding values of A, B, C, F, G, and H for the range of values of r in 0.4mm increments are shown Table I below.

TABLE I

| Apical Radius of Curvature | Constant Coefficients | | | Constant Exponents | | |
|---|---|---|---|---|---|---|
| | A | B | C | F | G | H |
| 6.9 | −.011 | .017 | −.0035 | 1.6 | 1.85 | 2.4 |
| 6.5 | −.0116 | .0177 | −.00403 | 1.5872 | 1.8372 | 2.3615 |
| 6.1 | −.0123 | .01848 | −.00462 | 1.5730 | 1.8231 | 2.3192 |
| 5.7 | −.01305 | .0193 | −.0052 | 1.559 | 1.809 | 2.2769 |
| 5.3 | −.014 | .0203 | −.006 | 1.54 | 1.79 | 2.219 |
| 4.9 | −.0151 | .0215 | −.0069 | 1.518 | 1.768 | 2.154 |
| 4.5 | −.0166 | .02313 | −.00813 | 1.4885 | 1.738 | 2.065 |
| 4.1 | −.01805 | .02476 | −.00935 | 1.459 | 1.709 | 1.9769 |
| 3.7 | −.01997 | .02687 | −.01095 | 1.4205 | 1.670 | 1.8615 |
| 3.5 | −.021 | .02801 | −.0118 | 1.4 | 1.65 | 1.8 |

The diameter of the convex anterior surface may range from 6 to 16 mm, while the diameter of the concave posterior surface may be varied, and is most preferably around 12.0 mm. A peripheral portion of the contact element on the concave posterior surface may include a secondary peripheral curvature and overall may be as large as 17 mm, with a diameter of 15.5 mm being preferred. Center thickness of the contact element may range from 1.5 mm to 10 mm.

Figure 4:
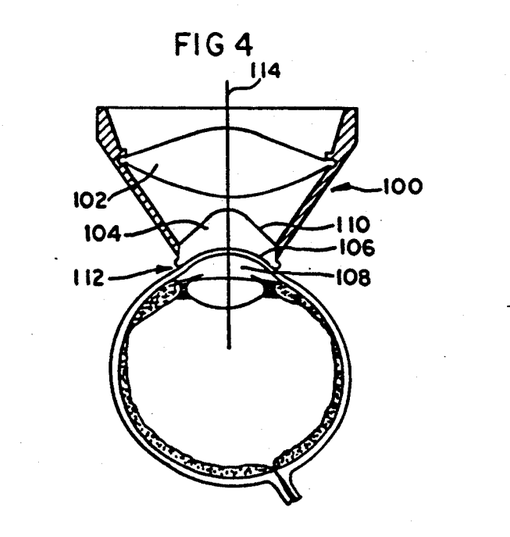
FIGS. 4 and 5 show translational movement of the lens system on an examined eye.
Figure 5:
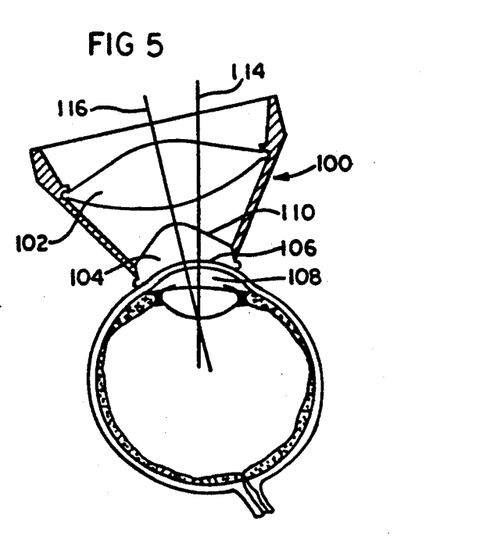

Turning now to FIGS. 4 and 5, an alternate embodiment of the design of the contact element is shown which facilitates translational movement of the lens on the cornea of the examined eye and provides additional advantages. In FIG. 4, the device 100 includes at least one anterior lens element 102 and a contact lens element 104 which is designed having an aspheric posterior concave surface 106. The concave posterior surface 106 of the contact element 104 is designed to closely approximate the aspheric contour of the cornea 108 of the examined eye over most of its surface. The concave posterior surface 106 of the contact element 104 is of prolate type, wherein the curvature decreases from the apex to the periphery of the lens. As seen at 112, it may be desirable to progressively flatten the peripheral slope of the surface so as to be equal or less than that of the average cornea at an equivalent diameter. By forming the surface in this manner, the device 100 functions as previously described to provide a condensing lens system for transmitting light from a light source onto the fundus of an eye as well as forming an aberration free, wide field image of the fundus when the device is on axis with the cornea of the eye at 114.

Additionally, the aspheric contact surface of the contact element 104 allows translational movement of the device 100 on the cornea surface with minimum localized peripheral lens bearing on the cornea. As seen in FIG. 5, translational movement of the device 100 to axis 116 is possible without incurring excessive localized lens bearing on the corneal surface 108 of the examined eye. It is also seen that the aspheric surface 106 generally maintains close contact with the cornea 108 throughout translational movement. The aspheric surface 106 of the contact element 104 will also function to inhibit the retention of bubbles between the contact element and the cornea of the eye which is a common problem in existing lens systems.

Figure 6:
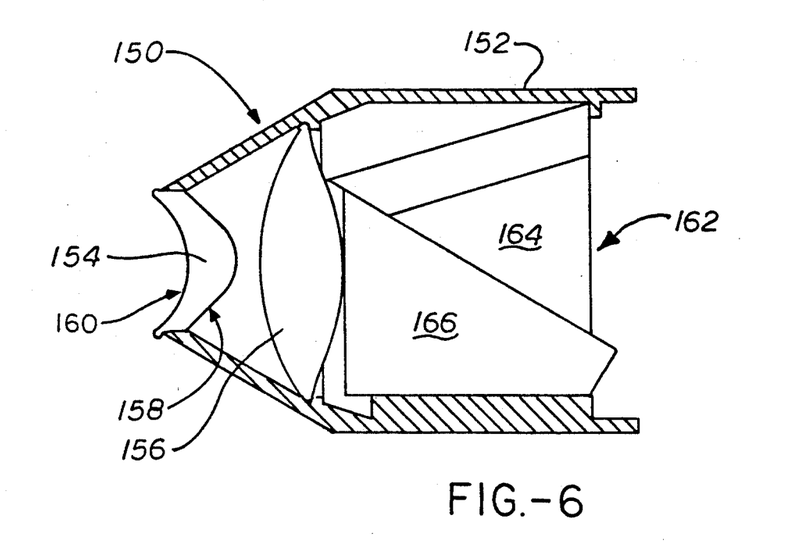
FIG. 6 is schematic plan view of an alternate embodiment of the indirect ophthalmoscopy diagnostic device which will form an upright aerial image of the fundus.

An alternate embodiment of the diagnostic indirect ophthalmoscopy device of the invention is shown in FIG. 6 wherein the device 150 includes a housing member 152 providing a means for securing and interconnecting a contact lens element 154 and at least one anterior lens element 156 in proper relationship to form an aerial image of the fundus of the eye as well as for condensing illuminating light onto the fundus in a manner similar to that previously described. The lens holding housing 152 allows digital manipulation of the device when disposed against the eye of a patient to facilitate observation of the fundus by an examining physician. The contact lens element 154 in this embodiment may again include an aspheric anterior surface 158 if desired, and may also include an aspherical posterior surface 160 which is matched substantially to that of the anterior surface of the average cornea. Again, both the posterior and anterior surfaces of the contact lens element 154 may be defined by the polynomial as described with reference to the embodiment of FIG. 1. The bi-convex anterior lens element 156 similarly may be provided with one or both surfaces thereof being aspherical and defined by the polynomial as described with reference to the anterior element of FIG. 1. Aspherizing the surfaces of the anterior element 156 may contribute to the minimization of aberrations to produce an image which is substantially free from aberrations such as field curvature, lateral astigmatism and distortion. As mentioned previously, one or both surfaces of the anterior lens element 156 may be spherical in shape, but combined with aspherical surfaces on the contact lens element or additional lens elements of the system to reduce excess peripheral power and associated optical aberrations.

In this embodiment of the invention, the device 150 also includes a reinverting prism structure generally indicated at 162, which may be a known configuration of a Pechan prism including two prism elements 164 and 166 which together function to erect the inverted image of the fundus produced by the image forming contact lens element 154 and anterior lens element 156. In this embodiment, the field of view obtainable by the device 150 may be limited by the erecting prism 162 such that it is desired to maximize the field of view obtainable by the device. To achieve the desired field of view, the image forming lenses comprising the contact lens element 154 and at least one anterior lens element 156 may have extremely high positive refractive power to provide significant light converging properties which will enable an extremely wide field of view for the system while providing optimum condensing and image forming properties.

As an example, in this embodiment, the contact lens element 154 may be a relatively thin, low power configuration, such as from 0 to 30 diopters or the like. In conjunction with a contact lens element of this type, the anterior lens element 156 may be a high powered lens element such as a 160–180 diopter lens. The contact lens 154 and anterior lens element 156 in combination may then contribute a desired amount of refractive power to achieve the desired field of view. It is apparent that the particular configuration of both the contact lens element 154 and anterior lens element 156 or additional anterior lens elements merely must be designed in conjunction with one another to provide the proper light converging characteristics necessary to achieve the optimum field of view in the system and can vary accordingly. When using high power lenses as shown in this embodiment, the relative spacing between the contact lens element 154 and any anterior lens elements 156 will necessarily be chosen such that the lens elements are coaxial with the eye and perpendicular to the optical pathway and spaced relative to one another so as to properly form the aerial image in an image plane anterior to the lens elements. The image formed by the lens elements of the device 150 will be a real image which is substantially free of aberrations, but which is an inverted image and undesirable for various examination or surgical techniques. The erecting prism structure 162 may thus erect the inverted image produced by the lens system of device 150 without degrading the quality of the image produced by the system. Viewing of the upright image formed by the device 150 using an ophthalmoscope or slit lamp biomicroscope may then be performed, with focusing on the image accomplished by positioning a microscope head of the biomicroscope to view the upright image which will essentially be formed in the plane of a surface within the erecting prism structure 162.

Figure 7:
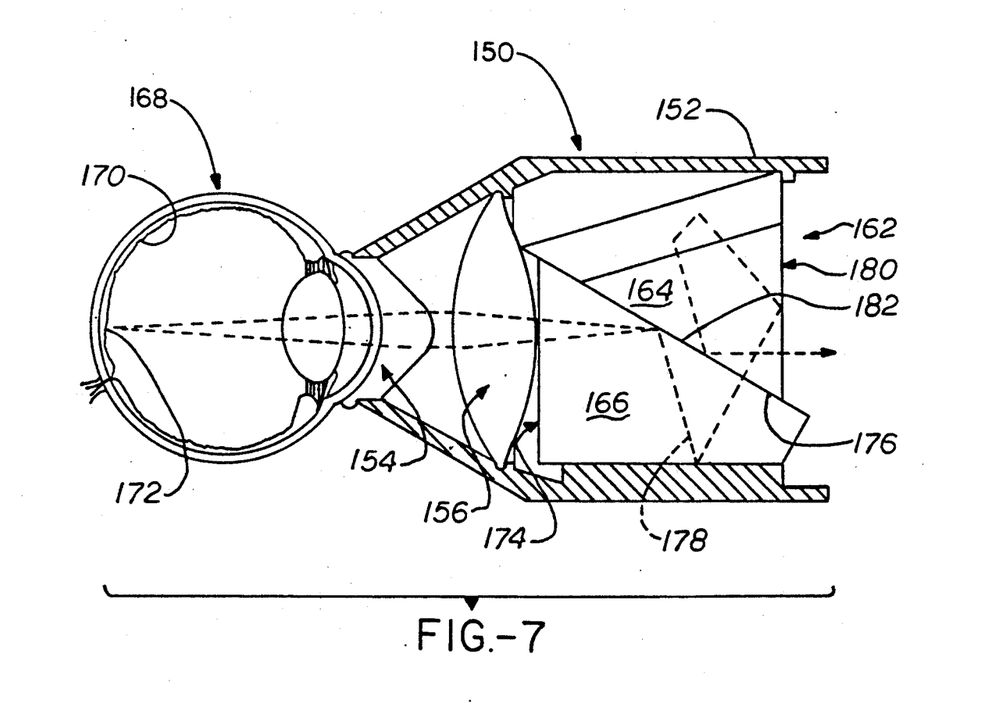
FIG. 7 shows the indirect ophthalmoscopy device of FIG. 6 in use for examination of an eye, and showing the light path through the device to form the upright aerial image of the fundus.

Turning now to FIG. 7, the light path through the optical device 150 to yield an upright aerial image of the fundus of an eye is shown in more detail. After illumination of the fundus 170 of eye 168, homocentric bundles of diverging light rays from the points in the illuminated fundus will be directed to pass through the pupil of the eye so as to emerge from the cornea as homocentric bundles of light rays. An example of the homocentric bundle of parallel light rays is shown from a single point at 172 on the fundus 170 of the eye 168, but it should be understood that a large number of homocentric bundles of parallel light rays will be produced from the fundus 170. As the light rays emerge from the cornea, they will be incident upon the back surface of the contact lens element 154 to be refracted thereby if contact lens element 154 is of positive refractive power. Upon exiting the contact lens element, the light rays will be incident upon the anterior lens element 156 wherein they will be further refracted to form an inverted real image of the fundus in the anterior focal plane of the anterior lens element 156. The inverted image is directed to the erecting prism structure 162 comprising elements 164 and 166.

In the embodiment as shown in these figures, a Pechan prism is utilized wherein the prism elements 164 and 166 are configured such that an image entering an entrance window 174 will be incident upon a surface 176 of the prism element 166 at an incidence angle so as to be reflected from this surface as indicated at 178. Surfaces of prism element 166 other than surface 176 may be mirrored such that the incident light rays 178 from surface 176 will be reflected back toward surface 176 at a proper incidence angle to pass through surface 176 into prism element 164. Light entering prism element 164 will be directed to an exit window 180 at an angle of incidence so as to be reflected off the surface and towards surfaces of prism element 164 wherein the image will essentially be erected to be incident upon surface 182 of prism element 164 at an incidence angle to be reflected outwardly of exit window 180 toward the viewing biomicroscope. The erecting nature of the prism structure as shown in the figure will thus produce an upright aerial image of the fundus as desired without degrading the quality of the image produced to any great extent.

Figure 8:
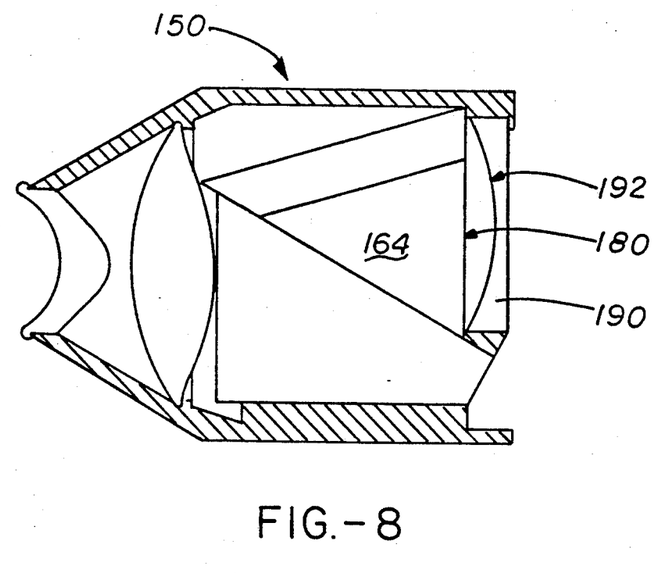
FIGS. 8 and 9 show schematic plan views of alternate embodiments of indirect ophthalmoscopy diagnostic devices which will form upright aerial images of the fundus.
Figure 9:
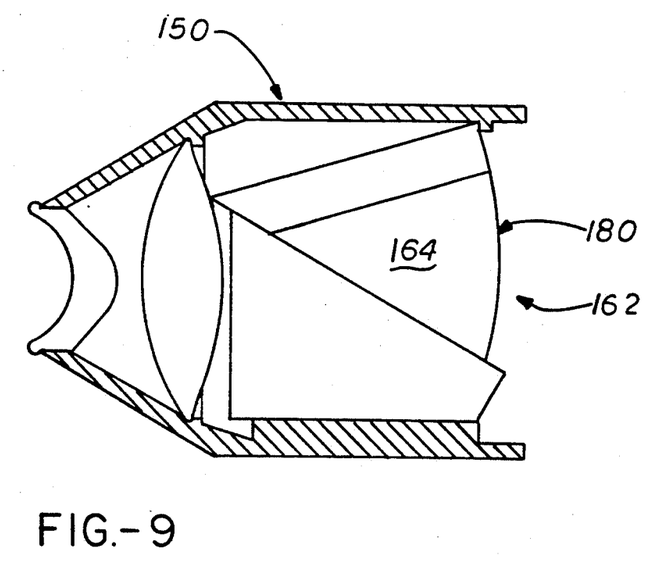

Turning now to FIGS. 8 and 9, alternate embodiments of the device as seen in FIG. 6 are shown to obtain an extremely wide field of view from the device. It was been recognized when utilizing an erecting prism structure such as the Pechan prism shown in this embodiment of the device that the field of view may be limited thereby. As the homocentric bundles of parallel light rays from the fundus are directed toward the erecting prism structure, only those which are properly incident upon the reflective surfaces of the prism structure will be erected and directed toward the biomicroscope. To enhance and facilitate examination of the fundus by means of the biomicroscope, it may be desirable to add divergence to the bundles of light rays exiting the erecting prism structure to more closely simulate the image size ordinarily achieved with an indirect ophthalmoscopic device. In this regard, the device 150 may further include an additional lens element 190 having a negative powered meniscus surface 192 which will add divergence to the homocentric bundles of light beams exiting the prism element 164 through exit window 180. The addition of negative refractive power to the system will act to slightly enlarge the formed upright aerial image of the fundus, and will additionally increase working distances relative to the biomicroscope to move the formed aerial image further from the device 150 toward the biomicroscope. In this way the examining physician will not be required to bring the biomicroscope head into close proximity with the device 150 and therefore the patient being examined so as to avoid any discomfort to the patient by close proximity of the microscope head. As seen in FIG. 9, an alternative embodiment accomplishing a similar goal may be provided by machining the exit window 180 of the prism element 164 so as to have a negative power meniscus which will add divergence to the exiting bundles of homocentric light beams therefrom. The effect of machining the exit window 180 will of course have to be taken into account in the erecting features of the prism structure 162 to achieve proper functioning of the device.

In the use of an erecting prism structure as shown in this embodiment of the invention, the erecting prism structure raises the possibility of producing reflections which may inhibit proper viewing of the formed image using the biomicroscope. In the normal use of an indirect ophthalmoscope or slit lamp biomicroscope, the source of illuminating light is associated with the biomicroscope, wherein illuminating light will be directed toward the examined eye from a location adjacent the microscope head. The illuminating light is thus made to pass through the optical device of the invention to be condensed onto the fundus of the eye as desired for proper illumination of the fundus. The problem thus arises that the illuminating light source by the biomicroscope could create reflections within the erecting prism elements which are desired to be avoided. Various alternative illumination techniques are available and have been used previously, such as transillumination techniques where light is directed through the sclera which diffuses the light for general illumination of the interior eye. Under normal circumstances, transillumination techniques do not provide the desired bright illumination of the fundus or other parts of the eye to form a bright aerial image by means of the indirect ophthalmoscopy device of the invention. Alternatively, the technique of endoillumination uses a source of illuminating light such as a strand or bundle of fiberoptic elements coupled to a light source which are surgically implanted within the eye so as to emit illuminating light directly onto the fundus for indirect ophthalmoscopy. With endoillumination techniques, which are commonly used in vitrectomy, no illuminating light passes through the indirect ophthalmoscopy device and no reflections can arise. The device will then act only as an image forming system, and will produce a sharp image of the fundus which will not be impaired by reflections in any manner. Although endoillumination techniques clearly avoid the production of reflections in the indirect ophthalmoscopy device, the necessity for surgically implanting the light source into the eye is certainly undesirable under many circumstances.

Figure 10:
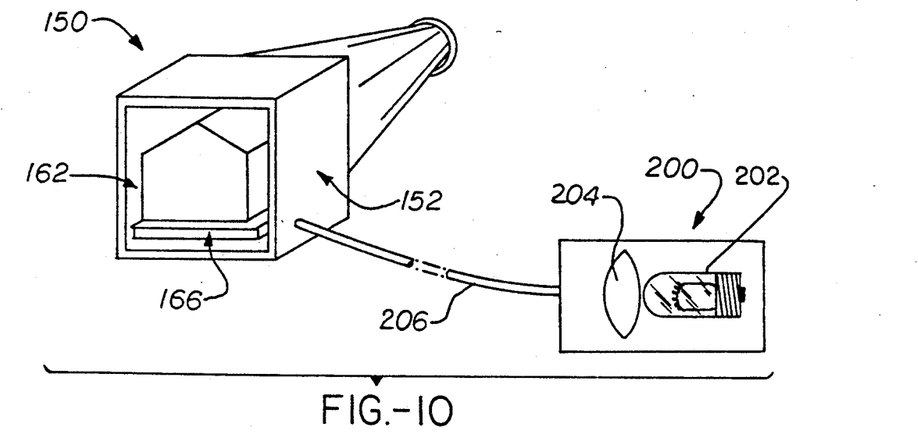
FIG. 10 shows the indirect ophthalmoscopy device of FIG. 6 having a separate means to illuminate the fundus of the eye to reduce reflections formed by the device.
Figures 11, 12:
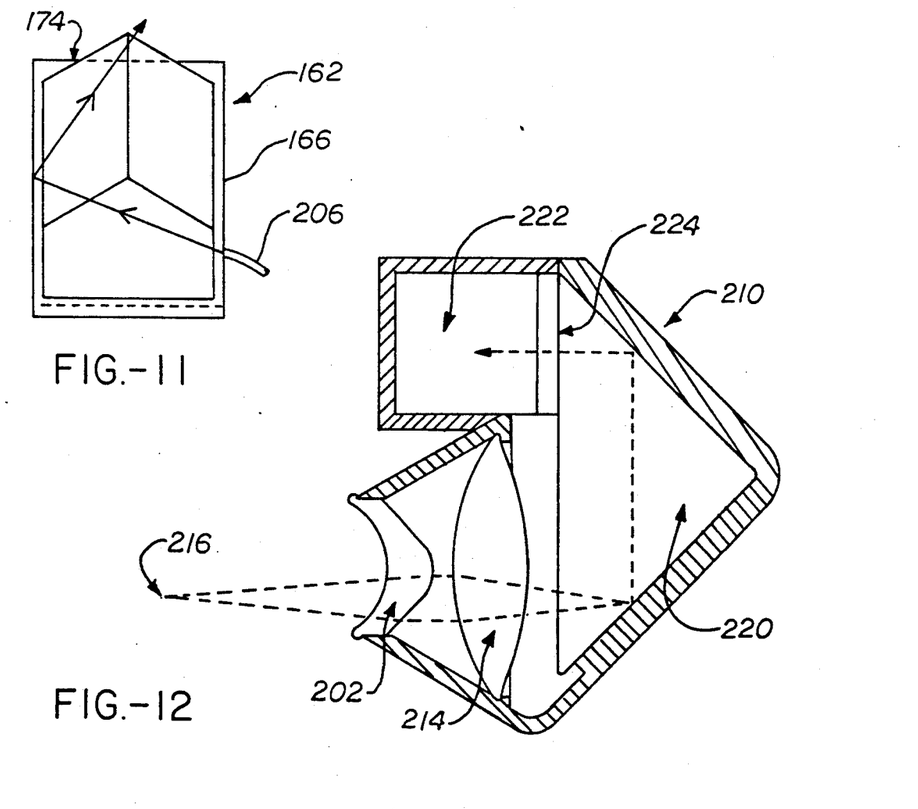
FIG. 11 shows a partial top plan view of the erecting prism used in the device of FIG. 10 showing the illuminating light path therethrough.
FIG. 12 is a schematic plan view of an alternate embodiment of the indirect ophthalmoscopy device which will form an upright aerial image of the fundus of an eye.

It is therefore an aspect of the invention to provide a separate illumination system associated therewith which will reduce the occurrence of reflections within the indirect ophthalmoscopy device. As seen in FIG. 10, the indirect ophthalmoscopy device 150 is shown to include a separate means for illumination 200 which may include a light source 202 and a condensing lens 204 which converges light from light source 202 into the entrance end of a fiberoptic strand or bundle 206. The opposite end of the fiberoptic strand 206 extends through housing 152 of the indirect ophthalmoscopy device to be attached in a position adjacent to the prism element 166 of the erecting prism structure 162. The mirrored side surface of prism element 166 may include a non-mirrored portion at the position of the fiberoptic cable end so as to admit light into the prism element 166 to be directed toward the fundus of the eye. As seen in FIG. 11, light from the fiberoptic strand 206 enters into prism element 166 at one side thereof through a non-mirrored portion of that side, wherein it will be directed toward the opposite side of prism element 166 to be reflected toward the entrance window 174 of prism element 166. The illuminating light will then proceed through the anterior lens element 156 where it will be converged to be incident upon the contact lens element 154 for further convergence onto the fundus of the eye as seen in FIG. 7. It should of course be recognized that a plurality of fiberoptic strands 206 may be provided to introduce light into the prism element 166 at various locations to provide full illumination of the fundus while minimizing reflections arising off the surfaces of the prism 162. For example, illuminating light may be introduced at the front face of prism element 166 or other similar locations so as to direct illuminating light to exit through the entrance window 174 of prism element 166 to be incident upon the lenses of the indirect ophthalmoscopy device. Reflections will be minimized as introduction of illuminating light into prism 162 is off-axis from the direction of viewing of the biomicroscope, resulting in significantly reduced scattering of light toward the microscope head.

Turning now to FIG. 12, an alternate embodiment of an indirect ophthalmoscopy device in accordance with the invention to form an upright image is shown. The device 210 again may include a contact lens element 212 and at least one anterior lens element 214, wherein homocentric bundles of diverging light rays from points such as point 216 of the illuminated fundus will be incident upon the lens elements 212 and 214 to be converged to form an inverted image of the fundus. Light from the image forming lenses 212 and 214 is then directed into an entrance window 218 of a first porro prism 220 being a narrow right angle prism. The first prism element 220 therefore will reflect incident light off a first angled surface opposite the entrance window 218 toward a second angled surface to direct the light out the opposite end of the entrance window 218 as seen in FIG. 12. A second prism element 222 which may be an identical porro prism is oriented at 90 degrees to the prism element 220 and situated such that it will accept the light exiting the first prism element 220 at an entrance window 224, where it will again be reflected off opposed angled surfaces to exit the second prism element 222 at the opposite end of entrance window 224 and toward the biomicroscope. The image of the fundus produced by the image forming lenses 212 and 214 will thus be erected and reverted by the combination of first and second porro prisms 220 and 222 in a known fashion. The image will be viewed by means of the biomicroscope offset from the actual location of the eye but will provide an upright image wherein the microscope head may simply be raised to view the image. The pair of porro prisms utilized in this embodiment will not degrade the image produced by the image forming lenses 212 and 214. It should be recognized that various prism structures may be utilized to form an upright erected image of the fundus which will be representative of the actual fundus being viewed. It is again possible to provide the prism elements with means whereby added divergence may be accomplished, or separate lenses to add divergence to the light rays forming the image to facilitate viewing of the image using the indirect ophthalmoscope or slit lamp biomicroscope.

It should also be apparent that in both of the embodiments of FIGS. 6 and 11, the image forming lenses may be positioned differently from that shown in the figures. For example, the anterior lens element of the devices may be positioned anterior of the reinverting prism structure or between the prism elements to accomplish similar convergence of the diverging bundles of light rays to form a clear and aberration free image of the fundus.

Figure 13:
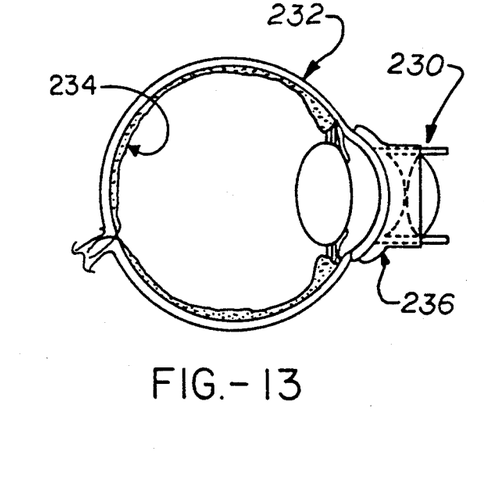
FIGS. 13 and 14 show another alternate embodiment of the indirect ophthalmoscopy device which is advantageously used to perform vitrectomy.
Figure 14:
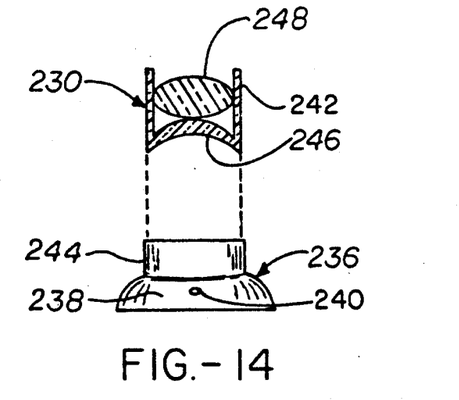

Turning now to FIGS. 13 and 14, a miniaturized indirect ophthalmic device 230 is shown positioned on the corneal surface of an eye 232 to produce an aerial image of the fundus 234 as desired. In this embodiment, the device 230 is adapted to fit into a vitrectomy ring 236 conventionally used in vitrectomy surgical procedures. The vitrectomy ring 236 comprises a flange portion 238 which is sewn directly onto the corneal surface by means of apertures 240 formed therein. The indirect ophthalmoscopy device 230 includes a housing 242 having a diameter slightly less than the diameter of the ring portion 244 of vitrectomy ring 236. The housing 242 will thus slip into the ring portion 244 to be held in place relative to the eye 232. The device 230 may include a contact lens element 246 which may conveniently be molded directly with the housing 242 or provided as a separate lens element. The contact lens element 246 includes a posterior surface which will contact the corneal surface of the eye when inserted into the vitrectomy ring 236, and will be maintained in this position without further manipulation by the examining physician. The device 230 may further include at least one anterior lens element 248 similar to that previously described, except that the device 230 being significantly smaller in its dimensional characteristics will require lens elements of suitable small size. To gain the proper field of vision, the anterior lens element 248 may be an extremely high powered lens such as a 160 or 180 diopter lens having small dimensions but producing a wide field of view. Again, the surfaces of both the contact lens element 246 and anterior lens element(s) may be aspherical to minimize aberrations and produce a clear distortion free image of the fundus. It should be recognized that once the device 230 is operatively positioned as shown in FIG. 13, no further manipulation of the device will be necessary and its position will be maintained in conjunction with the vitrectomy ring 236.

Figure 15:
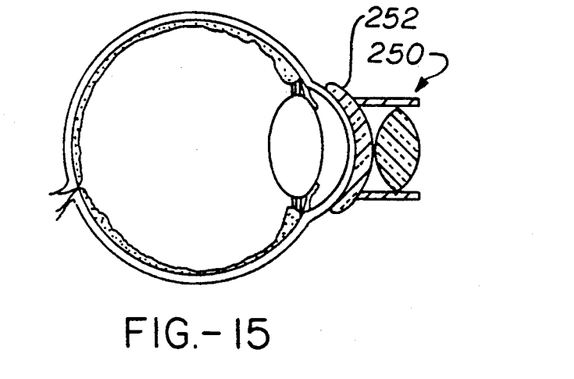
FIGS. 15 and 16 show another alternate embodiment of the indirect ophthalmoscopy device being a non-hand-held embodiment which will substantially maintain its position in relation to the eye for observation of the fundus by means of indirect ophthalmoscopy.
Figure 16:
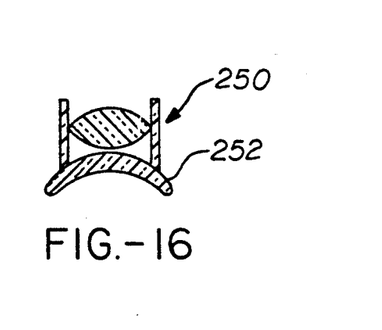

In FIGS. 15 and 16, a similar miniaturized indirect ophthalmoscopy device to that shown in FIGS. 13 and 14 is disclosed. In this embodiment, the device 250 is adapted to be positioned on the corneal surface of the eye, and will be maintained in this position by means of a large flange area 252 which will extend under the lid of the eye and be retained thereby. Although this embodiment will float to some degree on the eye, the provision of the flange 252 will essentially maintain its position without requiring digital manipulation by the examining physician. In other aspects, the device may be similar to that described with reference to FIGS. 13 and 14. In the embodiments of FIGS. 13-16, the indirect ophthalmoscopy device is a non-hand-held device which allows a higher degree of freedom for the examining physician, and which will provide a suitable field of view to view the whole retina through an undilated pupil for procedures such as vitrectomy or the like. The embodiments are extremely lightweight, and will therefore maintain their position on the examined eye to a great extent as desired. A reinverting or erecting structure may be utilized with these embodiments if desired, and these embodiments may be especially suitable for surgical procedures or photographic techniques.

Figure 17:
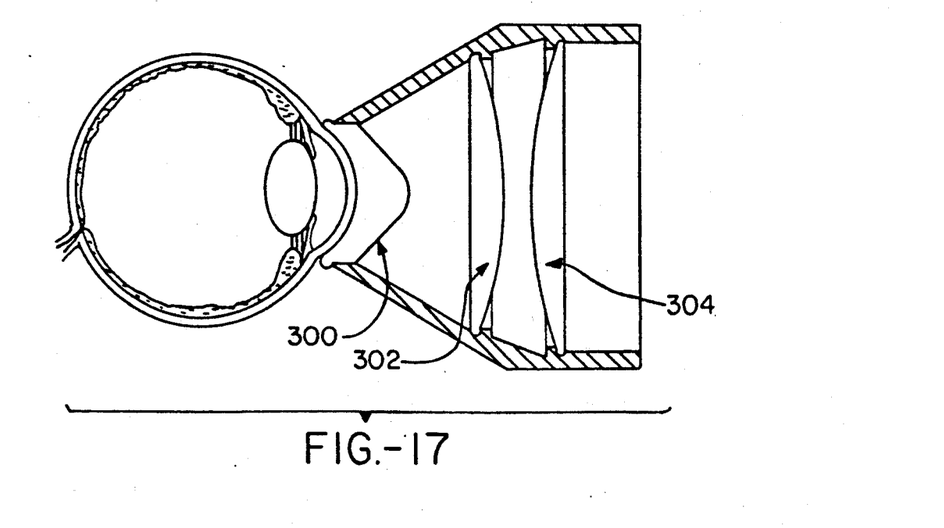

Turning now to FIG. 17, there is shown an alternate embodiment of the device which includes a contact lens element 300, which preferably will have an aspheric anterior surface defined by the polynomial as set forth previously. The posterior surface of the contact lens 300 may also be aspherical to match the contour of the aspheric cornea on which it is to be positioned. In this embodiment, a series of anterior lens elements are provided, which preferably will contribute to correction of refractive errors to yield the desired image forming and light condensing qualities as previously described. A first anterior lens element 302 may comprise a bi-convex or plano convex lens with at least one convex surface being the anterior surface of the lens. A second anterior lens element 304 may be of similar type as lens 302 except that its at least one convex surface is the posterior surface, which faces the convex anterior surface of lens element 302. The convex surfaces of the lens elements 302 and 304 may be spherical surfaces of revolution, wherein the combination of lens elements 302 and 304 yields significant corrective qualities. The combination of lens elements 302 and 304 may comprise a known Ramsden configuration which has been utilized in telescopic eyepieces. The Ramsden pair act in conjunction with one another to alleviate in part spherical aberrations which may be generated from the surfaces thereof. This configuration, in combination with an aspherical contact element may then provide the desired image forming and condensing qualities as described. The surfaces of the anterior lens elements 302 and 304 may also be aspherized if desired to further improve the optical properties of the device.

The diagnostic contact lens system for indirect ophthalmoscopy of the invention provides an optically superior condensing lens system and image forming system. The use of positive powered lens elements in the system as well as aspheric surfaces of revolution result in substantial correction of optical aberrations, lateral astigmatism and field curvature in an easily used, effective system. Although preferred embodiments of the invention have been described, it is to be understood that various modifications would be obvious to those skilled in the art and are embodied within the present invention as defined by the appended claims.

What is claimed is:

1. An indirect ophthalmoscopy lens device used to observe the fundus of the eye comprising,
   a holding means to support and position a plurality of lenses relative to one another,
   said plurality of lenses including a contact lens element having a concave posterior surface and convex anterior surface,
   at least one anterior lens element having first and second surfaces,
   said contact lens element and said at least one anterior, lens element being positioned relative to one another to refract light rays from an illumination system to form an image of the light source on the fundus of an examined eye and to collect light rays emerging from the fundus of the eye and refracting said emerging light rays to form an inverted aerial image of the fundus, and means supported within said holding means to erect said inverted image of the fundus produced by said contact lens element and said at least one anterior lens element to form a real erect image of the fundus anterior to said at least one anterior lens element.

2. The indirect ophthalmoscopy lens device of claim 1 wherein,
   said means to erect said inverted image is an erecting prism means wherein said inverted image will be incident upon said prism to be erected and thereafter viewed using an indirect ophthalmoscope or slit lamp biomicroscope.

3. The indirect ophthalmoscopy device of claim 2, wherein,
   at least one of said contact lens element or at least one anterior lens element has high positive refractive power to provide significant light converging properties which will enable a wide field of view to be achieved with use of said erecting prism means.

4. The indirect ophthalmoscopy device of claim 2, wherein,
   said erecting prism has an exit window through which the erect image may be viewed and has associated therewith a negative powered meniscus surface which will act to divert light rays passing therethrough so as to enlarge the upright image of the fundus.

5. The indirect ophthalmoscopy device of claim 4, wherein,
   said negative powered meniscus surface is provided by a lens element secured to said exit window of said erecting prism.

6. The indirect ophthalmoscopy device of claim 4, wherein,
   said negative powered meniscus surface is provided by forming the exit window of said erecting prism means as a negative powered meniscus surface.

7. An indirect ophthalmoscopy lens device used to observe the fundus of the eye comprising,
   a holding means to support and position a plurality of lenses relative to one another,
   said plurality of lenses including a contact lens element having a concave posterior surface and convex anterior surface,
   at least one anterior lens element having first and second surfaces,
   said contact lens element and said at least one anterior lens element being positioned relative to one another to refract light rays from a separate means for providing illuminating light associated with said device and adapted to illuminate the fundus of the eye to be examined, with said separate means for providing illuminating light providing a source of illuminating light in a direction off axis from the lens elements of the device to form an image of the light source on the fundus of an examined eye, and said lens elements also being adapted to collect light emerging from the fundus of the eye and refracting said emerging light rays to form an aerial image of the fundus to be examined.

8. The indirect ophthalmoscopy lens device of claim 7, wherein, said separate means of illuminating light is a light source and at least one fiber optic strand having first and second ends, wherein light from said light source is directed into said first end of said fiber optic strand and said second end is positioned within said holding means so as to emit light toward said eye to be examined.

9. An indirect ophthalmoscopy lens device used to observe the fundus of the eye comprising, a holding means to support and position a plurality of lenses relative to one another, said plurality of lenses including a contact lens element having a concave posterior surface and convex interior surface, at least one anterior lens element having first and second surfaces, said contact lens element and said at least one anterior lens element being positioned and supported relative to one another within said holding means, wherein said holding means is designed to enable positioning of said contact lens element on the corneal surface of the eye to be examined with said position being maintained on said corneal surface without hand manipulation of said holding means, wherein said lens elements act to refract light rays from an illumination system to form an image of the light source on the fundus of an examined eye and to collect light rays emerging from the fundus of the eye and refracting said emerging light rays to from an aerial image of the fundus.

10. The indirect ophthalmoscopy lens device of claim 9 wherein, said holding means said contact lens, and said at least one anterior lens element are designed to fit within a vitrectomy ring positioned on the corneal surface of the eye to be examined.

11. The indirect ophthalmoscopy lens device of claim 9 wherein, said holding means includes a flange portion designed to fit under the eyelid wherein said eyelid will maintain the position of said holding means on said eye.

12. An indirect ophthalmoscopy lens device for observing the fundus of the eye comprising, a holding means to support and position a plurality of lenses relative to one another, said plurality of lenses including a contact lens element having a concave posterior surface and convex anterior surface, said convex anterior surface of said contact lens being an aspheric surface of revolution defined by the polynomial expressed as follows:

$$y = (2rx + (e^2 - 1)x^2)^{\frac{1}{2}} + Ax^G + Cx^H$$

wherein r is the apical radius of curvature, e is the apical eccentricity, x is the distance from the apex of the surface along its axis of revolution, and A, B and C are constant co-efficients, and F, G and H are constant exponents, at least one anterior lens element having first and second surfaces, said contact lens element and said at least on anterior lens element being positioned relative to one another to refract light rays from an illumination system to form an image of the light source on the fundus of an examined eye and to collect light rays emerging from the fundus of the eye and refracting said emerging light rays to form an aerial image of the fundus.

13. The indirect ophthalmoscopy lens device of claim 12 wherein, two of said anterior lens elements are positioned relative to said contact element, each of which has at least one convex surface of revolution.

14. The indirect ophthalmoscopy contact lens of claim 12 wherein, said concave posterior surface of said contact element is an aspheric surface of revolution defined by said polynomial and is shaped to substantially conform to the shape of the anterior surface of the cornea of the eye to which said contact element is to be applied and to eliminate localized peripheral lens bearing during translational movement on said cornea.

15. The indirect ophthalmoscopy lens device of claim 13 wherein, said at least one convex surface of each of said anterior elements is a spherical surface of revolution, wherein said two anterior lens elements form a Ramsden lens configuration which acts to correct generated spherical aberrations from the individual spherical surfaces of each of said anterior lens elements.

16. The indirect ophthalmoscopy lens device of claim 13, wherein, said at least one convex surface of each of said anterior elements is an aspheric surface of revolutions defined by said polynomial.

17. The indirect ophthalmoscopy contact lens of claim 13, wherein, said at least one convex surface of each of said two anterior lens elements is positioned adjacent to the other of said anterior lens elements.

18. A device for observing the fundus of the eye under applied illumination comprising, a contact lens element having a convex anterior surface and a concave posterior surface, at least said anterior surface being an aspheric surface of revolution having a continuous and progressive variation in curvative peripheralward, said anterior surface being non-spherical over its extent, at least two anterior lens elements positioned relative to said two contact lens and along the same optical axis, said at least two anterior lens elements have at least one convex surface of revolution and wherein said at least one convex surface of each anterior lens element is positioned adjacent the other of said anterior lens elements, a holding means supporting said contact and anterior lens elements relative to one another, wherein light rays projected from a light source are converged through the device onto the fundus of the eye and emerge from the fundus to be refracted by the device to form an image of the fundus substantially free of optical aberrations.

19. The device of claim 12 wherein,
said posterior surface of said contact lens element is an aspheric surface of revolution.

20. The device of claim 13 wherein,
said contact and anterior lens elements have positive refractive power yielding significant light converging properties and producing an extremely wide field of view of the fundus of the eye.

* * * * *